(12) United States Patent
Shkolnikov et al.

(10) Patent No.: US 10,894,943 B2
(45) Date of Patent: Jan. 19, 2021

(54) VOLATILE ORGANIC COMPOUND TRANSPORT

(71) Applicant: Hewlett-Packard Development Company, L.P., Houston, TX (US)

(72) Inventors: Viktor Shkolnikov, Palo Alto, CA (US); Anita Rogacs, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 154 days.

(21) Appl. No.: 15/763,098

(22) PCT Filed: Oct. 27, 2015

(86) PCT No.: PCT/US2015/057611
§ 371 (c)(1),
(2) Date: Mar. 24, 2018

(87) PCT Pub. No.: WO2017/074319
PCT Pub. Date: May 4, 2017

(65) Prior Publication Data
US 2018/0273890 A1    Sep. 27, 2018

(51) Int. Cl.
| | | |
|---|---|---|
| C12M 1/00 | (2006.01) | |
| B01D 53/00 | (2006.01) | |
| C12M 1/34 | (2006.01) | |
| B01D 53/32 | (2006.01) | |
| B01D 67/00 | (2006.01) | |

(Continued)

(52) U.S. Cl.
CPC ............ *C12M 41/46* (2013.01); *B01D 53/32* (2013.01); *B01D 67/0086* (2013.01); *B01D 69/142* (2013.01); *B01D 69/145* (2013.01); *C12M 23/24* (2013.01); *C12M 41/12* (2013.01); *C12M 41/34* (2013.01); *G01N 33/54373* (2013.01); *B01D 2325/04* (2013.01); *G01N 33/54366* (2013.01)

(58) Field of Classification Search
CPC ...... C12M 41/34; C12M 29/24; C12M 41/30; C12M 29/06
See application file for complete search history.

(56) References Cited

U.S. PATENT DOCUMENTS 4,954,261 A * 9/1990 Alexandre ............. C12M 21/18
                                                                  210/321.75
6,947,132 B1   9/2005 Boss et al.
(Continued)

FOREIGN PATENT DOCUMENTS

GB     2319191      5/1998
JP     2006078274   3/2006
(Continued)

OTHER PUBLICATIONS

Kebarle, Paul et al., "From Ions in Solution to Ions in the Gas Phase", Analytical Chemistry, 1993, 65(22), 972A-986A.
(Continued)

*Primary Examiner* — Nathan A Bowers
(74) *Attorney, Agent, or Firm* — Rathe Lindenbaum LLP

(57) ABSTRACT

A lower chamber is to contain a culture that emits a volatile organic compound. A sensor is within an upper chamber. A transport accelerator/selector transports the volatile organic compound in the lower chamber towards the sensor.

19 Claims, 6 Drawing Sheets

(51) Int. Cl.
  *B01D 69/14*    (2006.01)
  *G01N 33/543*   (2006.01)
  *C12M 1/04*     (2006.01)

(56) References Cited

U.S. PATENT DOCUMENTS

| | | | |
|---|---|---|---|
| 2004/0142489 A1* | 7/2004 | Prohaska | G01N 1/2226 |
| | | | 436/181 |
| 2008/0068920 A1* | 3/2008 | Galliher | B01F 13/0827 |
| | | | 366/102 |
| 2008/0191153 A1* | 8/2008 | Marganski | C23C 14/564 |
| | | | 250/492.21 |
| 2008/0199904 A1* | 8/2008 | Suslick | C12Q 1/04 |
| | | | 435/34 |
| 2009/0239252 A1 | 9/2009 | Trevejo et al. | |
| 2011/0244543 A1* | 10/2011 | Larsen | B01J 19/006 |
| | | | 435/170 |
| 2013/0023435 A1 | 1/2013 | Kho et al. | |
| 2016/0266084 A1* | 9/2016 | Burge | G01N 33/1826 |

FOREIGN PATENT DOCUMENTS

| | | |
|---|---|---|
| JP | 2007525677 | 9/2007 |
| JP | 2010-246441 A | 11/2010 |
| JP | 2014219229 | 11/2014 |
| WO | WO-2015026297 A1 | 2/2015 |

OTHER PUBLICATIONS

Chang, A.S. et al.; "Detection of Volatile Organic Compounds by Surface Enhanced Raman Scattering"; Mar. 26, 2012.

Chung, Sang GWI et al., 'Volatile organic compound specific detection by electrochemical signals using a cell-based sensor', Journal of Microbiology and Biotechnology, 2008 vol. 18 No. 1 pp. 145-152.

Notingher I., "Raman Spectroscopy Cell-based Biosensors"; Jul. 26, 2007; http://www.mdpi.org/sensors/papers/s7081343.pdf.

Pasini, Patrizia et al., 'Use of a gas-sensor array for detecting volatile organic compounds (VOC) in chemically induced cells', Analytical and Bioanalytical Chemistry, 2004 vol. 378 No. 1 pp. 76-83.

Zhu, Jiangjiang et al., 'Fast detection of volatile organic compounds from bacterial cultures by secondary electrospray ionization-mass spectrometry', Journal of Clinical Microbiology, 2010 vol. 48 No. 12 pp. 4426-4431.

* cited by examiner

VOLATILE ORGANIC COMPOUND TRANSPORT

BACKGROUND

Biomedical research and medical diagnostics many times involves the growth of a cell culture, wherein the cells in the culture and their state are monitored. Such monitoring may be carried out by analyzing volatile organic compounds produced by the cells, the metabolic fingerprint of the cells.

DETAILED DESCRIPTION OF EXAMPLES

Biomedical research and medical diagnostics many times involves the growth of a cell culture, wherein the cells in the culture and their state are monitored. Such monitoring may be carried out by analyzing volatile organic compounds produced by the cells, the metabolic fingerprint of the cells. Unfortunately, sensing of the volatile organic compounds is often difficult due to slow transport of the volatile organic compounds to a sensing device and sensitivity issues with respect to the sensing device.

Figure 1:
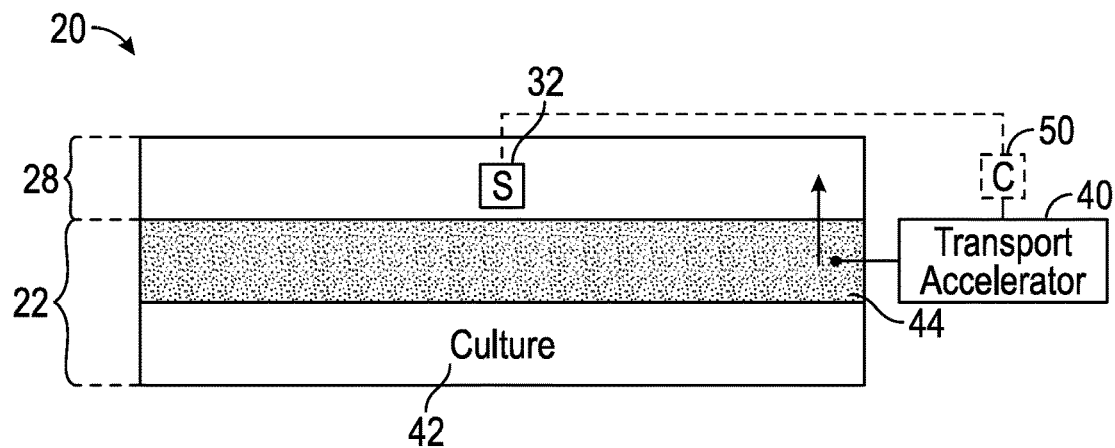
FIG. 1 is a schematic diagram of an example volatile organic compound sensing system.

FIG. 1 schematically illustrates an example volatile organic compound sensing system 20. As will be described hereafter, volatile organic compound sensing system 20 facilitates the identification of cells and the monitoring of their states by accelerating the transport of the volatile organic compounds to a sensor. System 20 comprises lower chamber 22, upper chamber 28, sensor 32 and transport accelerator 40.

Lower chamber 22 comprises a volume that is to contain a culture 42 that emits a volatile organic compound 44. Culture 42 comprises various cells in a growth medium. The growth medium facilitates growth of the cells, wherein the cells emit the volatile organic compounds 44. The growth medium may comprise a solid, such as a gel or liquid. Examples of culture 42 include, but are not limited to, cultures of *Escherichia coli*, *Pseudomonas aeruginosa*, *Klebsiella pneumonia*, *Staphylococcus aureus*.

Upper chamber 28 comprises a volume that is located vertically above lower chamber 22. Upper chamber 28 is separated from lower chamber 44 by a structure 29 that includes one or more openings or that is perforated so as to allows the transport of volatile organic compounds from lower chamber 22 to and into upper chamber 28. In one implementation structure 29 comprises a preferred baffle or framework. In another implementation, structure 29 comprises a permeable membrane. Upper chamber 28 receives the volatile organic compounds 44 emitted from culture 42. Upper chamber 28 contains sensor 32.

Sensor 32 comprises a device that senses a characteristic or multiple different characteristics of the volatile organic compounds 44 transported to upper chamber 28 and onto or in proximity with sensor 32. In one implementation, sensor 32 comprises a surface enhanced luminescence (SEL) sensor. In one implementation, sensor 32 comprises a surface enhanced Ramen spectroscopy (SER) sensor. For example, in one implementation, sensor 32 may comprise a metal surface or structure, wherein interactions between the analyte and the metal surface cause an increase in the intensity of the Raman-scattered radiation. Such metal surfaces may include a roughened metal surface, such as periodic gratings. In another implementation, such metal surfaces may comprise assemble nanoparticles. In some implementations, such metal surfaces may comprise metal islands. In one implementation, such metal islands comprise flexible columnar supports such as pillars, needles, fingers, particles or wires. In some implementations, the flexible columnar structures may include a metal cap or head upon which an analyte may be deposited. In some implementations, such columnar structures are formed from materials and/or are dimensioned so as to bend or flex towards and away from one another in response to applied electric fields. In some implementations, the SERS structures are movable and are self-actuating, wherein such columnar structures bend or flex towards one another in response to micro-capillary forces so as to self-organize, wherein such bending facilitates close spacing between the structures for greater scattered radiation intensity. In yet other implementations, sensor 32 may comprise other forms of sensors such as a gas chromatography sensor, a mass spectrometry sensor, and ion-molecule reaction mass spectrometry sensor and/or a colorimetric sensor.

Transport accelerator 40 comprises a device by which the volatile organic compounds 44 emitted by culture 42 are driven at an accelerated rate from lower chamber 22 to upper chamber 28 and sensor 32. Because the transport of the volatile organic compounds 44 to upper chamber 28 and sensor 32 is accelerated, characteristics of the volatile organic compound 44 may be more quickly identified are determined. Enhanced transport of the volatile organic compound to sensor 32 further enhances the efficiency and productivity of sensor 20. In applications where system 20 is being utilized to identify pathogens in the volatile organic compound 44, 20 facilitates the detection or identification of pathogens sooner in time so that targeted antibiotic treatment may be commenced sooner for enhanced treatment.

Transport accelerator 40 may have various constructions. As will be described hereafter, in one implementation, transport accelerator 40 may create an electric field that accelerates the transport of volatile organic compounds 44 to upper chamber 28 and sensor 32. In one implementation, the electric field directly ionizes the volatile organic compounds 44 (such as through corona discharge) and transports the volatile organic compounds 44 towards upper chamber 28 and the surfaces of sensor 32 via gas phase electrophoresis. In another implementation, the electric field utilizes electrospray phenomena to generate droplets of solution containing cellular metabolites, wherein the metabolites are carried towards the sensor surface.

In another implementation, transport accelerator 40 additionally or alternatively accelerates the transport of volatile organic compounds 44 to upper chamber 28 and sensor 32 by forming a thermal gradient between the lower chamber and the upper chamber. For example, in one implementation, transport accelerator 40 may form a thermal gradient between culture 42 and regions proximate sensor 32 and upper chamber 28. By heating culture 42 and maintaining sensor 32 or portions of upper chamber 28 at cooler, lower temperature, transport accelerator 40 generate a buoyancy flow of gas above culture 42 from culture 42 towards upper chamber 28 and sensor 32. The temperature gradient may also induce thermophoresis caused by the movement of particles or molecules in a temperature gradient due to changes in diffusion coefficient with the temperature. Such thermophoresis may also carry the volatile organic compounds 44 to sensor 32 to accelerate the transport of volatile organic compounds 44 and analytes toward sensor 32 so as to speed up the operation of system 20, accelerating diagnosis time.

As illustrated by broken lines in FIG. 1, in some implementations, system 20 may additionally comprise a controller 50. Controller 50 comprises a processing unit to control the operation of transport accelerator 40. In some implementations, controller 50 receives electrical power and selectively supplies electrical charge to transport accelerator 40. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 50 may be embodied as part of one or more application-specific integrated circuits (ASICs). Unless otherwise specifically noted, the controller is not limited to any specific combination of hardware circuitry and software, nor to any particular source for the instructions executed by the processing unit.

In implementations where system 20 is provided with controller 50, controller 50 may receive signals from sensor 32 indicating the characteristic or multiple characteristics of the volatile organic compounds 44. Based upon such characteristics, controller 50 may generate control signals adjusting the operation of transport accelerator 40 to adjust the rate at which volatile organic compounds 44 are being transported to upper chamber 28 and sensor 32. For example, controller 50 may adjust the rate at which volatile organic compounds 44 are being transported to upper chamber 28 by adjusting the intensity of the electric field and/or the magnitude of the thermal gradient. In one such implementation, controller 50 may utilize such closed-loop feedback to identify those operational parameters of transport accelerator 40 that most effectively enhance the acceleration of about organic compounds 44 to upper chamber 28 and sensor 32.

Figure 2:
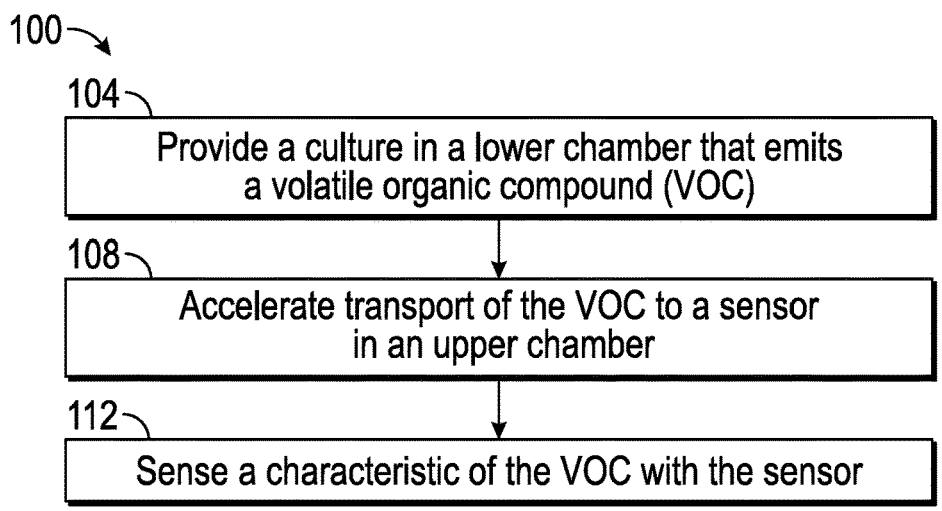
FIG. 2 is a flow diagram of an example volatile organic compound sensing method.

FIG. 2 is a flow diagram of an example method 100 for sensing a characteristic or multiple characteristics of a cell culture, such as cell culture 42. As indicated by block 104, a culture, such as culture 42, is provided in a lower chamber. The culture 42 emits a volatile organic compound, such as volatile organic compound 44.

As indicated by block 108, the transport of the volatile organic compounds 44 to a sensor, such a sensor 32, located in an upper chamber above the lower chamber 22 is accelerated. In one implementation, such acceleration is provided by a transport accelerator, such as transport accelerator 40 described above. As noted above, acceleration of the transport or movement of the volatile organic compounds may be achieved using an electric field or a thermal gradient to drive the volatile organic compounds 44 toward sensor 32.

As indicated by block 112, a sensor within the upper chamber 28 senses a characteristic of the volatile organic compounds. In one implementation, the sensor comprises a surface enhanced luminescence (SEL) sensor. In one implementation, the sensor comprises a surface enhanced Ramen spectroscopy (SER) sensor. In yet other implementations, the sensor comprises other forms of sensors such as a gas chromatography sensor, a mass spectrometry sensor, and ion-molecule reaction mass spectrometry sensor and/or a colorimetric sensor.

Figure 3:
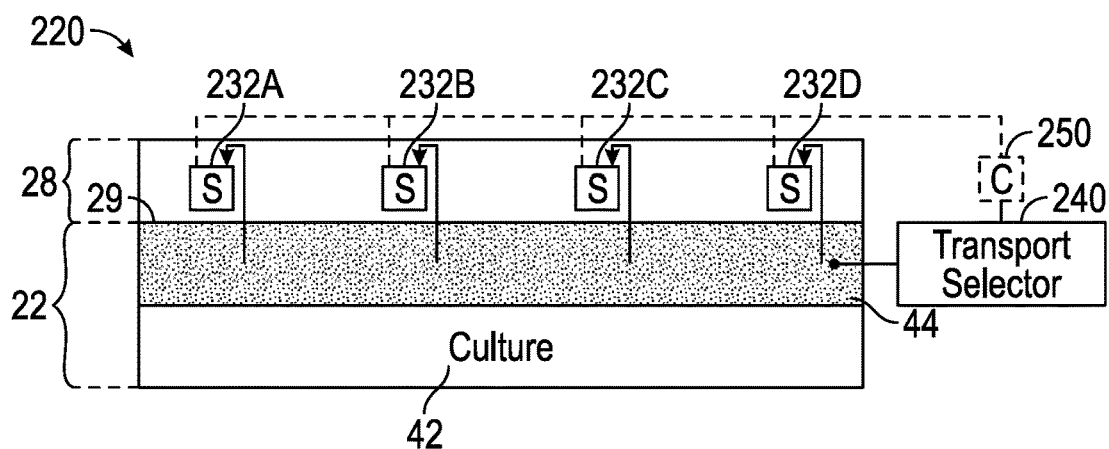
FIG. 3 is a schematic diagram of another example volatile organic compound sensing system.

FIG. 3 is a schematic diagram of volatile organic sensing system 220, another example volatile organic sensing system 20. System 220 is similar to system 20 except that system 220 comprises multiple sensors 232A, 232B, 232C and 232D (collectively referred to as sensors 232) in lieu of sensor 32 and comprises transports selector 240 in lieu of transport accelerator 40. Those remaining components or elements of system 220 which correspond to components or elements of system 20 are numbered similarly.

Sensors 232 are each similar to sensor 32 described above. As with sensor 32, each of sensors 232 is to detect a characteristic or multiple characteristics of volatile organic compounds. Sensors 232 are located at spaced apart locations within upper chamber 28. In one implementation, sensor 232 are different from one another in that each of sensors 232 is to detect a different type of characteristic of a volatile organic compound. In yet other implementations, sensor 232 are similar, but of different sensing resolutions. Although illustrated as a one-dimensional array within upper chamber 28, sensors 232 may alternatively be arranged in a two dimensional array or grid-like arrangement of sensors 232.

Transport selector 240 comprise a device that controls what volatile organic compounds 44 are transported to an individual sensor 232. In one implementation, transport selector 240 controls what volatile organic compounds 244 are transported to chamber 28 and sensors 232 and what volatile organic compounds 244 are blocked or hampered in their transport such that the volatile organic compounds do not reach any of sensors 232 or are substantially delayed with respect to other targeted volatile organic compounds. In one implementation, selector 240 blocks a portion of the total physical quantity of volatile organic compounds 244 to prevent or impede the transport of the total physical quantity of volatile organic compounds to chamber 28 and sensors 232. In other words, selector 240 controls the quantity of volatile organic compounds that are transported to each of the different sensors 232 such that even though the sensors 232 may receive the same type of volatile organic compounds, each of sensors 232 may receive different quantities of volatile organic compounds or receive the same volatile organic compounds at different rates. In one implementation, selector 240 blocks selected types of volatile organic compounds while facilitating or permitting the flow or transport of other selected types of volatile organic compounds to upper chamber 28 and sensors 232. In one implementation, transport selector 240 directs or channels different volatile organic compounds 44 (different volumes of volatile organic compounds or different types of volatile organic compounds) to different selected sensors 232. In the example illustrated, transport selector 240 may direct a first portion of the volatile organic compounds 44 to sensor 232A, a second portion of volatile organic compounds 44 to sensor 232B, a third portion of volatile organic compounds 44 to sensor 232C and a fourth portion of volatile organic compounds 44 to sensor 232D. In one implementation, each of the different portions comprise a different quantity or volume of the same volatile organic compounds. In another implementation, each of the different portions comprises or is composed of a different type of volatile organic compound. Each of the different portions of volatile organic compounds 44 emitted by culture 42 are biased towards a selected one of sensors 232. As a result, transport selector 240 may direct those volatile organic compounds to the particular one of sensors 232 most appropriate for detecting a selected or predetermined particular characteristic of such volatile organic compounds.

For example, during different stages of culture maturation or growth, different volatile organic compounds 44 may be released. At each of such different stages, transport differential 240 may direct the present volatile organic compounds to the particular one of sensors 232 that is most suitable for detecting the particular type of volatile organic compound being released at the particular stage. In yet other implementations, different volatile organic compounds may be concurrently emitted or released. Transport selector 240 operates such that different volatile organic compounds 44 are biased to different ones of sensors 232 most suitable for detecting the characteristics of each of the different volatile organic compounds 44.

Transport selector 240 may have various constructions. As will be described hereafter, in one implementation, transport selector 240 may comprise dividing walls or partitions extending between and separating the individual sensors 232 within upper chamber 28 to inhibit horizontal or transverse volatile organic compounds. In such an implementation, culture 42 may contain different cells that release different volatile organic compounds, wherein the different cells are aligned with the different partitioned regions such that the volatile organic compounds produced by first group of cells naturally rises or is naturally transported to the corresponding sent one of sensors 232 within the partition region. For example, those volatile organic compounds emitted by the cells below sensor 232B may be contained by the dividing walls such that, most, if not all, of the volatile organic compounds emitted are produced by the cells below sensor 232B are directed to sensor 232B while those volatile organic compounds produced by the cells below sensor 232D may be contained by the dividing walls such that, most, if not all, of the volatile organic compounds emitted are produced by the cells below sensor 232D are directed to sensor 232D. The same channeling applies for the remaining ones of sensors 232.

In another implementation, transport selector 240 may vertically block the transport of selected volatile organic compounds such that only selected volatile organic compounds are allowed to pass upper chamber 28 and sensors 232. For example, in one implementation, transport selector 240 may comprise a permeable membrane that selectively allows certain selected volatile organic compounds to pass through while at the same time blocking or impeding the flow or transport of other untargeted volatile organic compounds. In one implementation, different membranes may be employed below different sensors 232 such that different sensors 232 receive different volatile organic compounds. In one implementation, both the aforementioned dividing walls and multiple different membranes may be employed to differentiate what volatile organic compounds are transported to each of the different sensors 232.

In yet other implementations, transport selector 240 may also serve as a transport accelerator, wherein different volatile organic compounds are accelerated at different rates, if at all, to different sensors 232. For example, in one implementation, transport selector 240 may create different electrical fields, either different in time or different in location, wherein the different electrical fields differently accelerate the transport of different volatile organic compounds 44 to different sensors 232. In yet another implementation, transport selector 240A creates different thermal gradients, either different in time or different in location, wherein the different thermal gradients differently accelerate the transport of different volatile organic compounds 44 to different sensors 232.

As illustrated by broken lines in FIG. 3, in some implementations, system 220 may additionally comprise a controller 250. Controller 250 comprises a processing unit and associated non-transitory memory containing instructions for directing the operation of the processing unit. In such an implementation, controller 250 may receive signals from each of sensor 232 indicating the characteristic or multiple characteristics of the volatile organic compounds 44. Based upon such characteristics, controller 250 may generate control signals adjusting the operation of transport selector 240 to adjust the rate and/or direction at which volatile organic compounds 44 are being transported to upper chamber 28 and sensors 232.

For example, controller 250 may adjust the rate at which volatile organic compounds 44 are being transported to one particular sensor 232 as compared to another one of sensors 232 by adjusting the intensity of the electric field and/or the magnitude of the thermal gradient being applied respect to one of sensors 232 as compared to the other of sensors 232. For example, in response to sensing a slow rate of the volatile organic compound reception at a particular one of sensors 232, controller 250, to increase the reception of volatile organic compounds at the sensor 232 having the slower rate of reception, may output control signals causing transport selector 240 to increase the thermal gradient or increase the electric field in the region corresponding to the sensor 232 having the slower rate of volatile organic compound reception.

Figure 4:
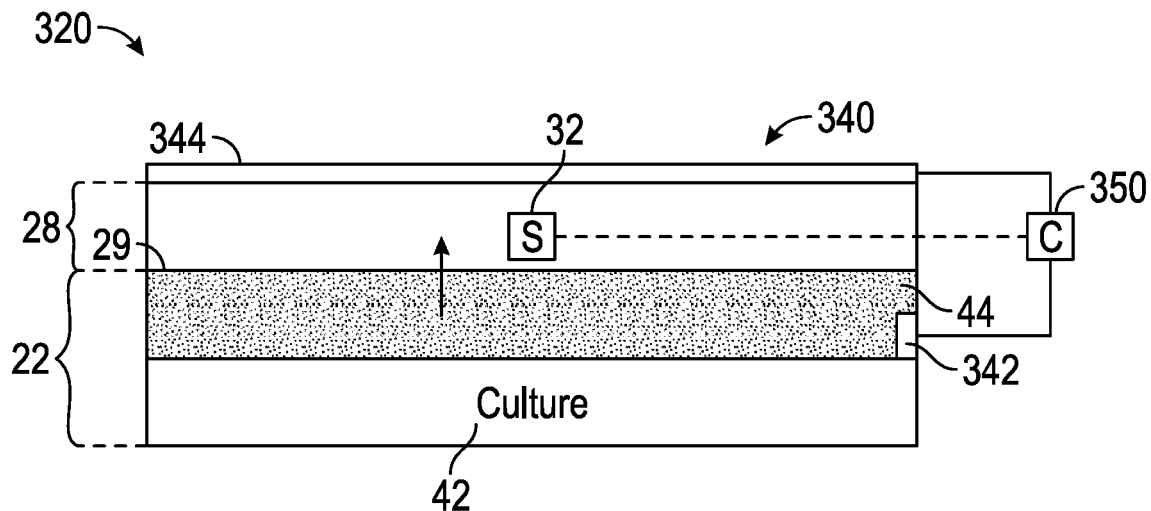
FIG. 4 is a schematic diagram of another example volatile organic compound sensing system.

FIG. 4 is a schematic diagram illustrating volatile organic compound sensing system 320, an example implementation of system 20. System 320 is similar to system 20 except that system 320 is specifically illustrated as comprising transport accelerator 340, a particular implementation of transport accelerator 40. The remaining components or elements of system 320 which correspond to components or elements of system 20 are numbered similarly.

Transport accelerator 340 accelerates the transport of volatile organic compounds produced by culture 42 to upper chamber 28 and sensors 32 by applying an electric field. In one implementation, the electric field directly ionizes the volatile organic compounds 44 (such as through corona discharge) and transports the volatile organic compounds 44 towards upper chamber 28 and the surfaces of sensor 32 via gas phase electrophoresis. Transport accelerator 340 comprises electrodes 342, 344 and controller 350.

Electrode 342 comprises an electrically conductive plate, rod or other electrically conductive structure located within lower chamber 22 so as to extend above culture 42. In one implementation, 342 is positioned along a side wall lower chamber 22. Electrode 344 comprises an electrically conductive plate, rod or other electric conductive structure located within upper chamber 28. In one implementation, electrode 344 comprise an electrically conductive plate along a top or ceiling of upper chamber 28. In other implementations, electrode 344 may be situated along a side wall of upper chamber 28, about sensor 32 or integrated as part of sensors 32. Electrodes 342, 344 cooperate to form an electric field that accelerates the transporter movement of volatile organic compounds 44 and an upward direction from above culture 42 to upper chamber 28.

Controller 350 comprises a processing unit and associated non-transitory memory containing instructions for directing the operation of the processing unit. Controller 350 selectively applies to charge to one or both of electrode 342, 344 so as to form the electric field between electrodes 342 and 344. In one implementation, the electric field formed between electrodes 342 and 344 comprise an electric field of between $10^4$ V/m and $10^6$ V/m, and nominally $10^5$ V/m.

As indicated by broken lines, in one implementation, controller 350 also function similar to controller 50 described above. In such an implementation, controller 350 receives signals from sensor 32 indicating characteristics or parameters of the sensed volatile organic compound and/or the rate at which the volatile organic compounds are being sensed or received by sensors 32. Based on such feedback, controller 350 may adjust the timing and/or intensity of the electric field between electrodes 342, 344 to adjust, increment or decrement, the rate at which the volatile organic compounds 44 are being accelerated to sensor 32. For example, in response to sensing a slow rate of VOC transport to sensor 32, controller 350 may increase the intensity, duration and/or frequency electric field to increase the rate at which the volatile organic compounds are transported to sensors 32. Alternatively, at predetermined times when the rate of VOC emission by the cells themselves is low, controller 350 may lower the intensity, duration and/or frequency of the electric field, delaying accelerated transport until a sufficient quantity of volatile organic compounds are present for transport and sensing.

Figure 5:
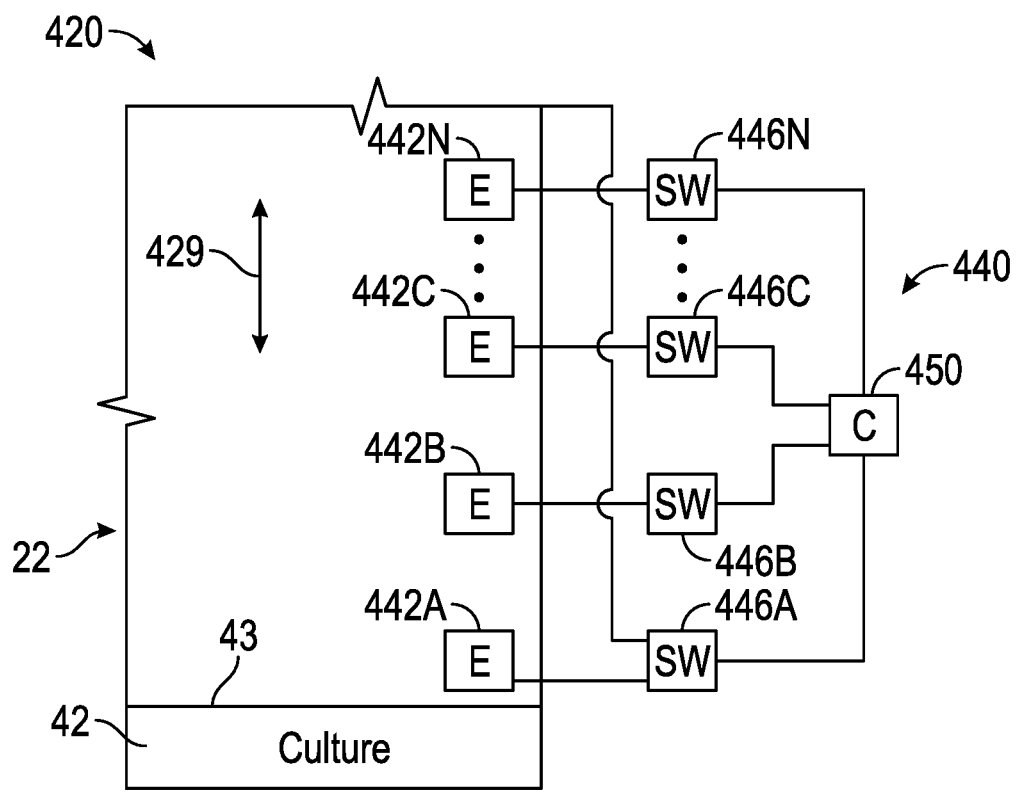
FIG. 5 is a schematic diagram of another example volatile organic compound sensing system.

FIG. 5 schematically illustrates volatile organic compound sensing system 420, another example of system 20. System 420 is similar to system 320 described above except that system 420 comprises transport selector 440 in lieu of transport accelerator 340. As with system 320, system 420 comprises lower chamber 22 and upper chamber 28 separated by structure 29, sensor 32 and electrode 344 (each of which is shown in FIG. 4). Those components or elements of system 420 are shown in FIG. 5 and which correspond to components or elements of system 320 are numbered.

As with transport accelerator 340, transport selector 440 accelerates the transport of volatile organic compounds 44 from lower chamber 22 two upper chamber 28 and sensors 32. Transport selector 440 differently transports different volatile organic compounds 44 to upper chamber 28 and sensors 32 at different rates. In the example illustrated, transport selector 440 comprises a series or one-dimensional array of electrodes 442A, 442B, 442C . . . 442N (collectively referred to as electrodes 442), switches 446A, 446B, 446C . . . 446N (collectively referred to as switches 446) and controller 450.

Electrodes 442 comprise electrically conductive plates, rods or other electric conductive structures vertically spaced along lower chamber 22 at locations in close proximity to, but above culture 42. In some implementations, some electrodes 442 may extend below the surface of culture 42, wherein such electrodes are not employed, but may be employed in other circumstances where the surface of culture 42 is lower.

In one implementation, the electrode closest to the surface of culture 42, electrode 442A, is spaced from the surface 43 of culture 42 by distance less than or equal to 1 mm and nominally less than or equal to 5 cm. Electrodes 442 are vertically spaced from one another, in the direction indicated by arrows 429, by distance D of less than or equal to 3 cm. In one implementation, electrodes 442 have a uniform vertical spacing. In another implementation, those electrodes 442 have a varying or non-uniform spacing. For example, in one implementation, electrodes 442 closer to surface 43 of culture 42 may have a closer spacing with respect to one another as to compared to those electrodes 442 more distant from surface 43.

Switches 446 comprise devices by which electrodes 442 may be selectively turned on, turned off or activated. In one implementation, switches 446 selectively connect each of the respective electrodes 442 to a source of electrical power or charge in response to control signals from controller 450. In one implementation, each of switches 446 comprises a transistor.

Controller 450 comprises a processing unit and associated non-transitory memory containing instructions for directing the operation of the processing unit. Controller 450 outputs control signals to selectively activate switches 4462 selectively charge an individual one of electrodes 442 or a selected subset or portion of electrodes 442 so as to differently transport different volatile organic compounds 44 to sensor 32 in upper chamber 28. For example, in some implementations, the volatile organic compounds 44 emitted by culture 42 may have different degrees of diffusivity such that the volatile organic compounds rise from culture 42 at different rates to different heights above surface 43 of culture 42. Controller 450 may selectively charge the individual one of electrodes 442 to target the particular type of volatile organic compound at a particular height above surface 43 of culture 42 for accelerated transport to sensor 32.

For example, a particular type of volatile organic compound produced by culture 42 and being targeted may diffuse to a height proximate to electrode 442C at a particular time or stage, whereas a non-targeted volatile organic compound concurrently produced by culture 42 may diffuse to a height proximate to electrode 442A. By selectively using and charging electrode 442C, rather than electrodes 442A or electrodes 442B controller 450 may accelerate the transport of the targeted volatile organic compound to sensor 32 while the natural transport of the volatile organic compound proximate to sensor 442A is not accelerated and therefore either remains within lower chamber 44 or is not transported in time for sensing to sensor 32.

Figure 6A:
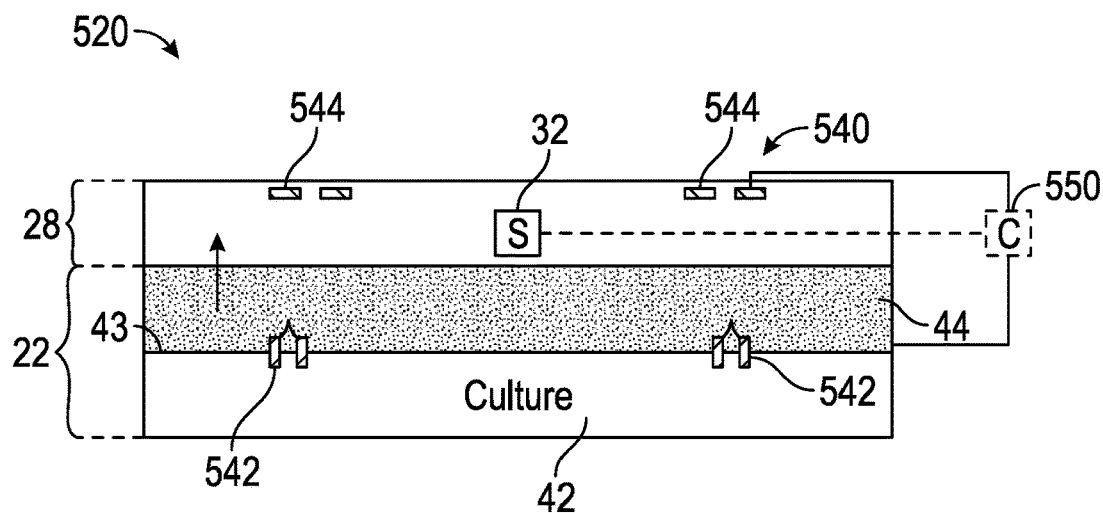
FIG. 6A is a schematic diagram of another example volatile organic compound sensing system.
Figure 6B:
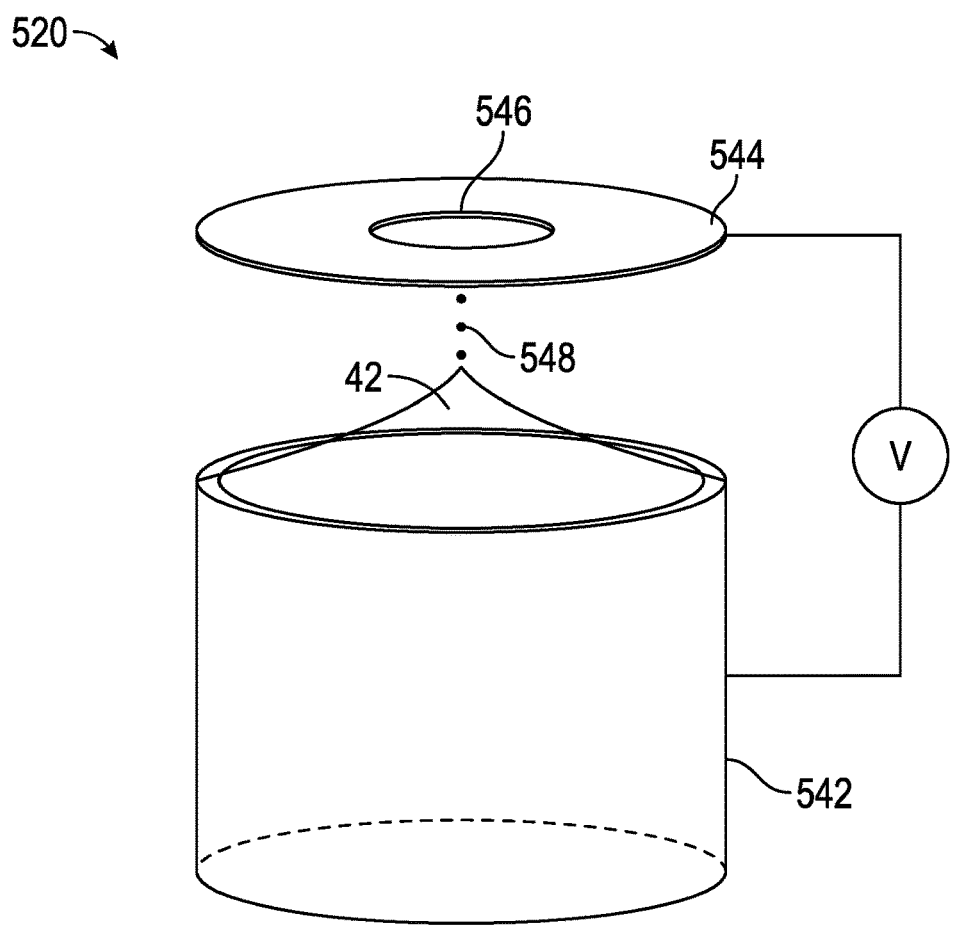
FIG. 6B is a diagram of an example electrode pair of the example volatile organic compound sensing system of FIG. 6A.

FIGS. 6A and 6B schematically illustrate volatile organic compound sensing system 520, another example implementation of sensing system 20. System 520 is similar to system 20 except that system 520 is specifically illustrated as comprising transport accelerator 540, another implementation of transport accelerator 40. The remaining components or elements of system 520 which correspond to components or elements of system 20 are numbered similarly.

Transport accelerator 540 accelerates the transport of volatile organic compounds produced by culture 42 to upper chamber 28 and sensors 32 by applying an electric field. In the example illustrated, transport accelerator 540 utilizes an electrode in the form of capillaries placed on the surface of the culture 42 in combination with a counter electrode to generate droplets of solution containing the analyte or volatile organic compounds, through electrospray phenomena, to facilitate such volatile organic compounds being carried to upper chamber 28 and sensor 32. Transport accelerator 540 comprises electrodes 542, 544 and controller 550.

Electrodes 542, 544, upon the creation of an electric field between such electrodes, causes the surface of culture 42 to break up into charged droplets pursuant to electrospray phenomena. FIG. 6B illustrates an example pair of electrodes 542, 544 and the electrospray phenomena. As shown by FIG. 6B, electrodes 542 comprise capillaries or tubes located within lower chamber 22 (as shown in FIG. 6A) across, below or at the surface 43 of culture 42. Electrodes 544 comprise plates or other structures vertically above electrodes 542 and having apertures 546. Electrodes 542 and 544 cooperate to form an electric field that draws the solution of culture 42 upwards to form charged droplets 548 which are accelerated towards upper chamber 28 and sensor 32.

In one implementation, electrodes 544 are located within upper chamber 28. In one implementation, electrodes 544 are located above sensor 32. In other implementations, electrodes 544 may be located within lower chamber 28, vertically above electrodes 542.

Controller 550 comprises a processing unit and associated non-transitory memory containing instructions for directing the operation of the processing unit. Controller 550 selectively applies to charge to one or both of electrodes 542, 544 so as to form the electric field between electrodes 542 and 544. In one implementation, the electric field formed between electrodes 542 and 544 comprise an electric field of between $10^5$ V/m and $10^7$ V/m, and nominally $10^6$ V/m.

As indicated by broken lines, in one implementation, controller 550 also function similar to controller 50 described above. In such an implementation, controller 550 receives signals from sensor 32 indicating characteristics or parameters of the sensed volatile organic compound and/or the rate at which the volatile organic compounds are being sensed or received by sensors 32. Based on such feedback, controller 550 may adjust the timing and/or intensity of the electric field between electrodes 542, 544 to adjust, increment or decrement, the rate at which the volatile organic compounds 44 are being accelerated to sensor 32. In implementations where system 520 comprises multiple electrodes 542 and/or multiple electrodes 544, controller 550 may adjust the number of electrodes 542, 544 that are electrically charged to create electric fields, thereby adjusting the amount of charged droplets 548 that are produced in the rate at which volatile organic compounds or the analytes are transported to upper chamber 28 and sensor 32.

For example, in response to sensing a slow rate of VOC transport to sensor 32, controller 550 may increase the intensity, duration, frequency and/or number electric fields to increase the rate at which the volatile organic compounds are transported to sensor 32. Alternatively, at predetermined times when the rate of VOC emission by the cells themselves is low, controller 550 may lower the intensity, duration and/or frequency of the electric field, delaying accelerated transport until a sufficient quantity of volatile organic compounds are present for transport and sensing.

Figure 7:
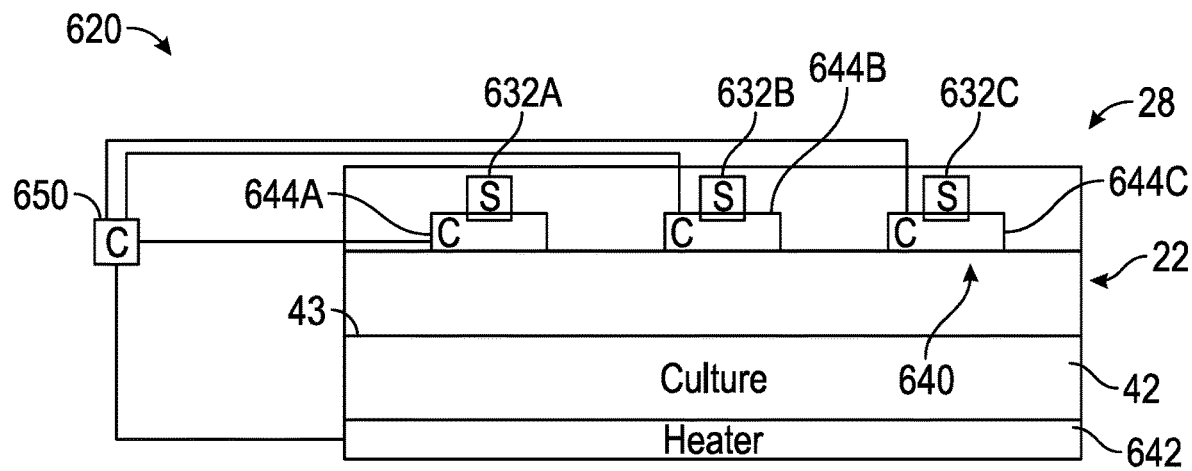
FIG. 7 is a schematic diagram of another example volatile organic compound sensing system.

FIG. 7 schematically illustrates volatile organic compound sensing system 620, an example implementation of system 20 as well as system 220. Sensing system 620 is similar to sensing systems 20 and 220 except that system 620 is specifically illustrated as comprising transport selector 640, a specific implementation of transport selector 240. Transport selector 640 also serves as a transport accelerator, similar to transport accelerator 40. Those components or elements of system 620 which correspond to components or elements of systems 20 and 220 are numbered similarly.

As shown by FIG. 7, system 620 comprises lower chamber 22 and upper chamber 28, were lower chamber 22 is to contain a culture 42. System 620 additionally comprises multiple sensors 632A, 632B and 632C (collectively referred to as sensors 632). Each of 632 are similar to sensor 32 described above. As with sensor 32, each of sensors 632 is to detect a characteristic or multiple characteristics of volatile organic compounds. Sensors 632 are located at spaced apart locations within upper chamber 28. In one implementation, sensor 632 are different from one another in that each of sensors 632 is to detect a different type of characteristic of a volatile organic compound. In yet other implementations, sensor 632 are similar, but of different sensing resolutions. Although illustrated as a one-dimensional array within upper chamber 28, sensors 632 may alternatively be arranged in a two dimensional array or grid like arrangement of sensors 632.

Transport selector 640 comprises a device that controls what volatile organic compounds 44 are transported to an individual sensor 632. Transport selector 640 accelerates the transport of volatile organic compounds 44 to upper chamber 28 and sensors 32 by forming a thermal gradient between the lower chamber and the upper chamber. In the example illustrated, transport selector 640 comprises temperature control elements proximate to culture 42 and sensors 32. In the example illustrated, transport selector comprises heater 642 and cooling devices 644A, 644B, 644C (collectively referred to as cooling devices 644).

Heater 642 comprises a heating device within or adjacent to lower chamber 22 two generate and apply heat to culture 42 or to the space within lower chamber 22 above culture 42. In the example illustrated, heater 642 is located below culture 42. In other implementations, heater 642 may be located along the sides or chamber 22 below or above surface 43 of culture 42. In one implementation, heater 642 comprises an electrically resistive heater.

Cooling devices 644 comprise devices that withdraw heat or cool a surrounding region. One example of such a cooling device 644 is a Peltier cooler. In another implementation, cool fluid may be distributor transported to withdraw heat from the region thereby cool the region. In the example illustrated, each of sensors 632 has an associated cooling device 644, facilitating selective cooling of regions about individual sensors 632. In one implementation, each going device 644 comprises a ring or other structure encircling or surrounding the associated sensors 632.

Controller 650 comprises a processing unit and associated non-transitory memory containing instructions for directing the operation of the processing unit. Controller 650 selectively controls heater 642 and cooling devices 644 to create a thermal gradient between heater 642 and cooling devices 644. In one implementation, the thermal gradient formed between heater 642 and an activated cooling device 644 is between 10 and 1000 K/m and nominally 100 K/m. In one implementation, culture 42 is heated to a temperature of 37° C. while the regions of or about an activated sensors 632 is cooled to a temperature of 32° C. The thermal gradient generate a buoyancy flow of gas above culture 42 from culture 42 towards upper chamber 28 and sensors 632. Such buoyancy flow carries about organic compounds towards sensors 632 to accelerate their transport. In implementations where the surface of sensor 32 itself is, the volatile organic compounds 44 may condensate onto the sensor surface itself which in turn promotes physiosorption and chemisorption of the volatile organic compounds to the sensor surface. The temperature gradient further induces thermophoresis, the movement of particles or molecules an attempt to gradient due to changes in diffusion coefficients with temperature. Such thermophoresis also carries volatile organic compounds to the sensor surface. Such acceleration mechanisms enhance the transport of analytes or volatile organic compounds to sensors 632 to speed up the operation of system 620.

Controller 650 may further bias or influence the rate at which different sensors 632 receive volatile organic compounds or analyte. In one implementation, controller 650 independently controls each of cooling devices 644 to form different thermal gradients between each of the different sensors 632 and heater 642. In one implementation, controller 650 may actuate one of cooling device 644 while the remaining cooling devices for remain off or an active. In doing so, controller 650 may accelerate transport of volatile organic compounds to the specific sensor 632 proximate the activated cooling device 644, increasing the rate at which the sensor proximate the activated cooling device 644 receives analyte or volatile organic compounds as compared to the other sensors 632. In other implementations, controller 650 may actuate the different cooling devices 644 two different cooling states such that different thermal gradients are formed between heater 642 and the different cooling devices 644 such a different VOC transport rates or acceleration rates are established respect to the different sensors 632.

In one implementation, controller 650 may generate control signals such that sensors 632 sequentially sense volatile organic compounds over time. Cooling devices 644 may be sequentially activated such that volatile organic compounds are accelerated, sequentially over time, to the different sensors 632. For example, sensors 632 may be different from one another in that the different sensors are specially configured to sense different volatile organic compounds or are configured to provide different sensing resolutions or sensitivities. In such an implementation, controller 650 may first actuate cooling device 644A during an early stage of culture growth such that the early produced VOCs are transported, in a larger proportion, to sensor 632A which is better configured or equipped to sense such early produced VOCs. During a later stage of culture growth, controller 650 may inactivate cooling device 644A and activate cooling device 644B such that the later produced VOCs are transported, in a larger proportion or percentages, to sensor 632B which is better configured or equipped to sense later produced VOCs.

Figure 8:
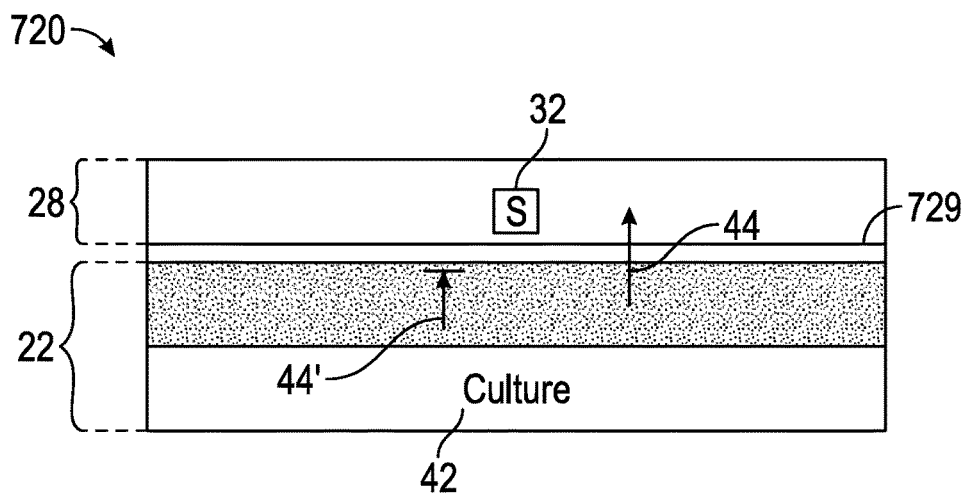
FIG. 8 is a schematic diagram of another example volatile organic compound sensing system

FIG. 8 schematically illustrates volatile organic compound sensing system 720, an example implementation of system 220. System 720 comprises lower chamber 22, upper chamber 28, sensor 32 and gas permeable membrane 729. The gas permeable membrane 729 extends between lower chamber 22 and upper chamber 28. The gas permeable membrane 729 selectively allows certain targeted volatile organic compounds 44 to be transported to upper chamber 28 and sensor 32 while blocking other non-targeted volatile organic compounds 44'. Membrane 729 facilitates the use of a complex mixture of VOCs such that individual sectors may detect and quantify only those target analytes in the mixture. Permeable membrane 729 further delays certain volatile organic compounds from reaching sensor 32 to facilitate reading a time history of the release of volatile organic compounds. By preventing or blocking certain volatile organic compounds 44', membrane 729 facilitates detection of a single analyte's spectrum. As a result, quantification of the fraction of volatile organic compounds 44 in the original mixture is simplified by reducing deconvolving of the individual spectra from the convolved spectrum of the mixture. Examples of materials for permeable membrane 729 include, but are not limited to, polytetrafluoroethylene, polycarbonate, nylon, polyacetate, cellulose acetate, polyester, polypropylene, polyethersulfone, polyacrylonitrile, polyvinylidene fluoride, glass fiber, and mixed cellulose ester.

Figure 9:
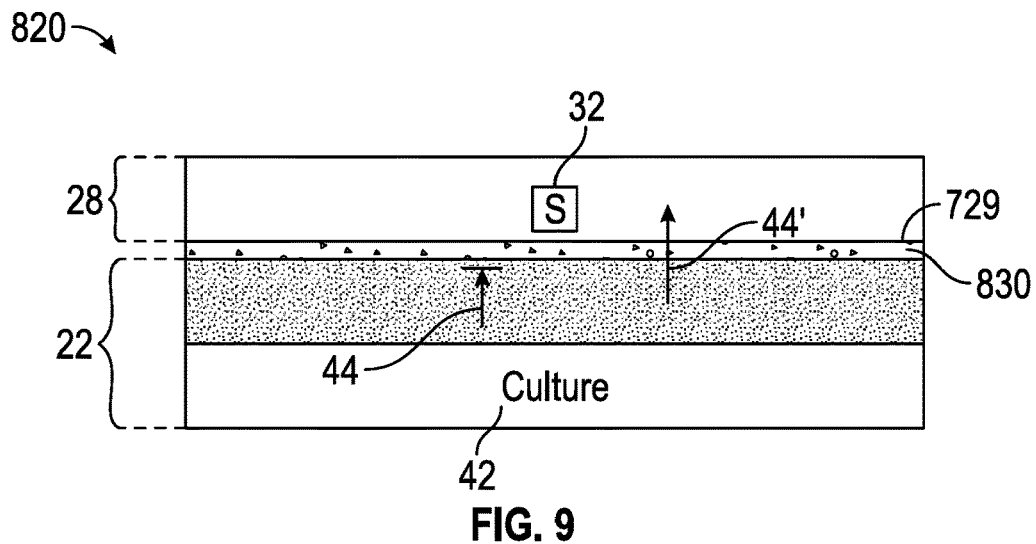
FIG. 9 is a schematic diagram of another example volatile organic compound sensing system.

FIG. 9 schematically illustrates volatile organic compound sensing system 820, another implementation of system 220 described above. System 820 is similar to system 720 except that system 820 additionally comprises reactive elements 830 carried by or impregnated within permeable membrane 729. Those remaining components or elements of system 820 which correspond to elements or components of system 720 are numbered similarly.

Reactive elements 830 comprise catalysts or reactive chemical species that convert volatile organic, 44 passing through membrane 729 to a different chemical state or to a different compound. In one implementation, reactive elements 830 convert volatile organic compounds 44 produced by the cells of culture 42 into analytes or other volatile organic compounds that are better detectable by sensor 32 than their precursors. In some implementations, reactive elements 830 are used to remove non-targeted or interfering species from the volatile organic compound mixture to better facilitate detection of analytes of interest or target analytes in the mixture. Such reactive elements 830 may increase the sensitivity and selectivity of system 820. Examples of reactive elements that may be impregnated into or supported by membrane 729, include, but are not limited to, palladium (e.g., for general hydrogenation), platinum (e.g, for amine hydrogenation), iridium (e.g., for fully substituted olefin hydrogenation). For example, these may include particles, nanoparticles, or chelated atoms of these compounds.

Figure 10:
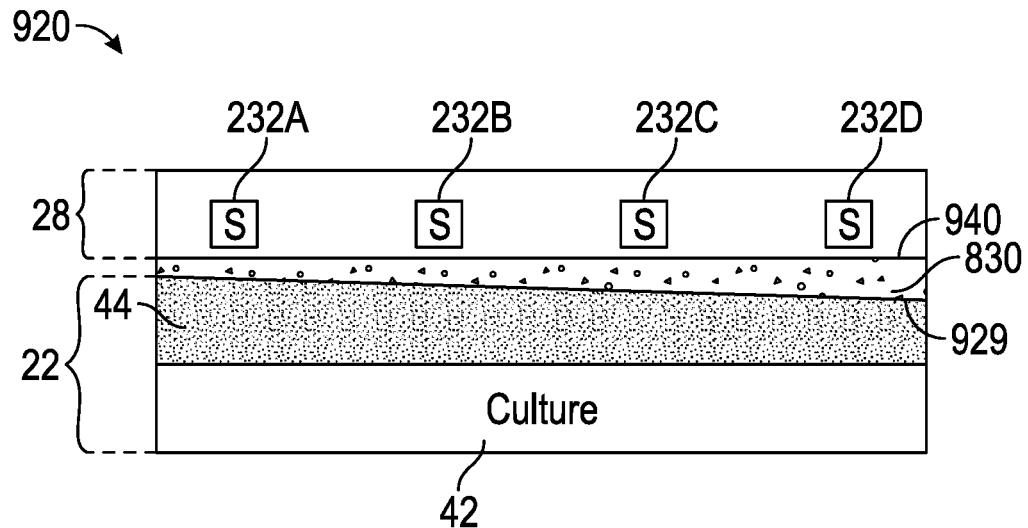
FIG. 10 is a schematic diagram of another example volatile organic compound sensing system.

FIG. 10 schematically illustrates volatile organic compound sensing system 920, another example implementation of system 220 described above. System 920 is similar to system 220 except that system 920 is specifically illustrated as comprising transport selector 940, a particular implementation of transport selector 240. Transport selector 940 comprises a semi permeable membrane 929 across and between lower chamber 22 and upper chamber 28. In the example illustrated, membrane 929 additionally comprises reactive elements 830 described above. In other implementations, reactive elements that relate 30 may be omitted.

Membrane 929 has a varying thickness across over lower chamber 22. In the example illustrated, membrane 929 has a gradually changing, ramping or sloping change in thickness below sensors 232, across lower chamber 22 and culture 42. In other implementations, membrane 929 may have a stepped change in thickness below sensors 232 and across lower chamber 22 and culture 42. The varying thickness of membrane 929 results in the transport of volatile organic compounds 44 upwards through membrane 929 to vary. As a result, different sensors 232 receive volatile organic compounds 44 at different rates over time. The thickness gradient across the array of sensors 232 may result in the sensors proximate to the thinner regions of membrane 929 (232A in the example) to receive volatile organic compounds far earlier than those sensors adjacent to thicker regions of membrane 929 (sensor 232D in the example). As a result, the history of the release of volatile organic compound production or release over time may be tracked using the signals from sensors 232 of system 920.

Figure 11:
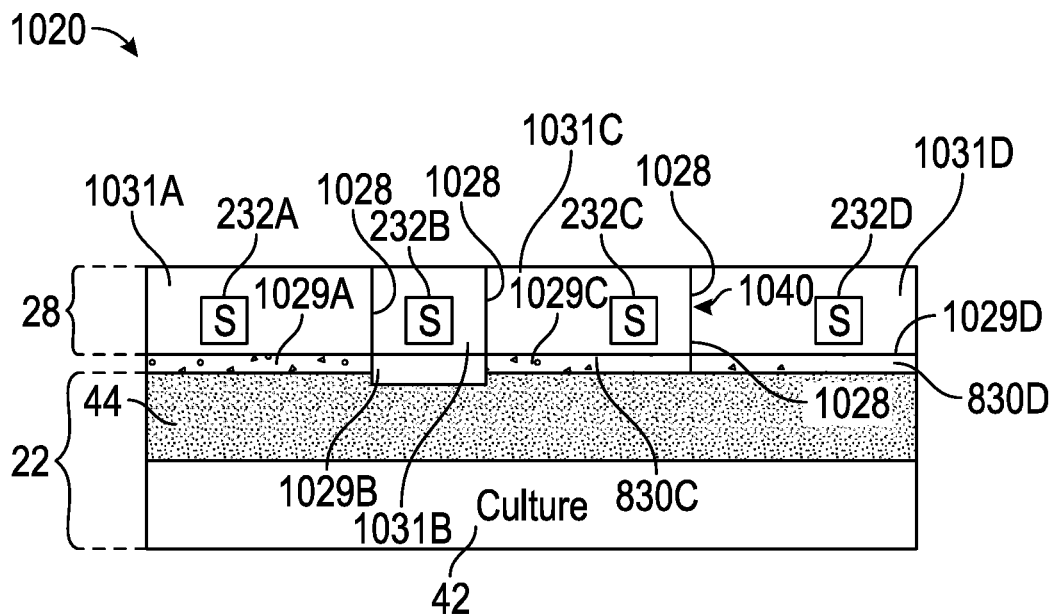
FIG. 11 is a schematic diagram of another example volatile organic compound sensing system.

FIG. 11 schematically illustrates volatile organic compound sensing system 1020, another example implementation of system 220. System 1020 is similar to system 220 except that system 1020 is specifically illustrated as comprising transport selector 1040, a specific implementation of transport selector 240. Those components or elements of system 1020 correspond to components or elements of system 220 are numbered similarly.

Transport selector 1040 comprises partitions 1028 and gas permeable membranes 1029A, 1029B, 1029C and 1029C (collectively referred to as membranes 1029). Partitions 1028 comprise divider walls extending within upper chamber 28 between consecutive sensors 232. Partitions 1028 compartmentalized upper chamber 28 into sub chambers or compartments 1031A, 1031B, 1031C and 1031D, respectively, to contain sensors 232A, 232B, 232C and 232D, respectively. In one implementation, partitions 1028 are gas impermeable so as to inhibit the flow of VOCs within one of compartments 1031 to a different one of compartments 1031. In some implementations, partitions 1028 may comprise gas selective permeable membranes, allowing certain gases to pass across such partitions 1028. Partitions 1028 form such compartments 1031, facilitating multiplex diagnostic assays lower diagnostic cost per assay.

Membranes 1029 are each similar to membrane 729 described above. Each of membranes 1029 is aligned with an associated compartment 1031 or an associated subset or group of compartments 1031. In the example illustrated, each of compartments 1031 has an associated different membrane 1029. In other implementations, a subset of the compartments may share a same membrane 1029.

Membranes 1029 facilitate the transport or passage of different VOCs and/or VOCs at different rates to their respective associated sensors 232. In the example illustrated, membrane 1029S and membrane 1029B have different thicknesses. In one implementation, membranes 1029A and 1029B are formed from different materials having different gas permeation are gas passed through characteristics. In the example illustrated, membranes 1029A and 1029B are not impregnated or do not carry reactive elements 830 while membranes 1029C and 1029D carry or are impregnated reactive elements. In the example illustrated, membrane 1029C is impregnated with or carries a first reactive element 830C all membrane 1029D is impregnated with or carries a second reactive element 830D that is different than the first reactive element 830D. As a result, each of sensors 232 receives VOCs at different rates or VOCs that have been differently altered by different reactive elements 830.

As noted above with respect to system 220, in one implementation, sensors 232 may be different from one another. Such an implementation, different ones of sensors 232 may be customized to sense a particular type of analyte or volatile organic compound as compared to other ones of sensors 232. Although each compartment 1031 is illustrated as comprising a single sensor 232, in other implementations, each of compartments 1031 may contain multiple sensors or a grid or array of sensors in some implementations, the membrane associated with or underlying an individual compartment containing multiple sensors 32 may have a varying thickness similar to that described above with respect to system 920.

Figure 12:
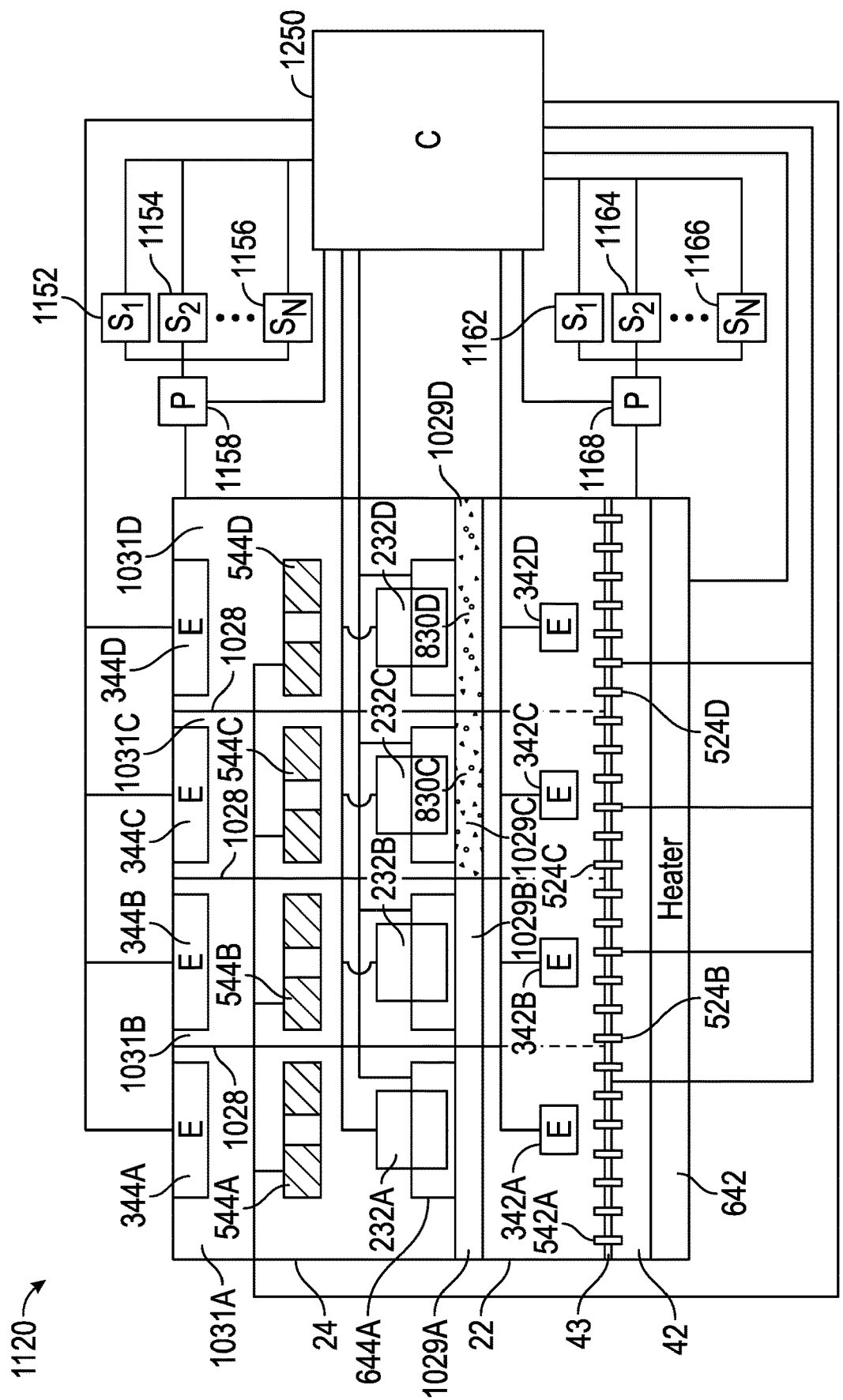
FIG. 12 is a schematic diagram of another example volatile organic compound sensing system.

FIG. 12 schematically illustrates volatile organic compound sensing system 1120, another example implementation of systems 20 and 220. Those components of volatile organic compound sensing system 1120 which correspond to components of any of the above described volatile organic compound sensing systems are numbered similarly. As shown by FIG. 12, system 1120 comprises a system that combines many of the above described sensing features in a single sensing system.

System 1120 comprises lower chamber 22, upper chamber 24, sensors 232A, 232B, 232C, 232D, electrodes 342A, 342B, 342C, 342D (collectively referred to as electrodes 342), electrodes 344A, 344B, 344C, 344D (collectively referred to as electrodes 344), electrodes 542A, 542B, 542C, 542D (collectively referred to as electrodes 542), electrodes 544A, 544B, 544C, 544D (collectively referred to as electrodes 544), heater 642, cooling devices 644A, 644B, 644C, 644D, partitions 1028, membranes 1029A, 1029B, 1029C and 1029D, gas sources 1152, 54, 1156, pump 1158, culture media sources 1162, 1164, 1166, pump 1168 and controller 1250. Each of electrodes 342 is similar to electronic 342 described above and each of electrodes 344 is similar to electrode 344 described above with respect to system 320 except that each of the compartments 1031A, 1031B, 1031C and 1031D formed by partitions 1028 contains a pair of electrodes comprising one of electrodes 342 and one of electrodes 344. As a result, controller 1250 may selectively output control signals to selectively and independently actuate each electrode pair to selectively form an electric field for accelerating the transport of volatile organic compounds to a particular one of sensors 232 and in particular one of compartments 1031. In one implementation, each of electrodes 342 comprise a series of individual electrode elements extending at different heights above surface 43 of culture 42 as described above with respect to electrodes 442 in system 420. In such an implementation, controller 1250 selectively charges one of the electrode elements to accelerate the transport of different volatile organic compounds based upon the different diffusivities or heights above surface 43.

Electrodes 542 and 544 are similar to electrodes 542 and 544 described above with respect to system 520 except that electrodes 542 and 544 are grouped into independently controllable or actuatable subsets or pairs. The subset or pair is actuatable independent of the other subsets or pairs. As a result, controller 1250 may selectively and independently actuate electrode pairs to selectively accelerate the transport of volatile organic compounds to an individual one of sensors 232 contained within a particular compartment 1031. For example, controller 1250 may selectively actuate electrodes 542A and 544A to accelerate the transport of volatile organic compounds to sensor 232A while the remaining electrodes 542 and 544 are not charged. In another implementation, controller 1250 may apply different electrical charges to create different intensity electrical fields in the different pairs of electrodes 542, 544 to vary the rate at which electrospray droplets are formed and vary the rate at which the analyte or volatile organic compounds are transported to the respective sensors 232 in the respective departments 1031.

Heater 642 and cooling devices 644 are controlled by controller 1250 in a fashion similar to as described above with respect to system 620. Likewise, membranes 1029 selectively transmit volatile organic compounds to the respective compartments 1031 and/or alter the chemical nature of the volatile organic compounds being transported through the use of reactive elements 830C and 830D as described above with respect to system 1020. In one implementation, system 1120 provides a user with the option to select one of multiple available modes by which system 1120 may operate. For example, a user may choose to accelerate and differentiate the transport of volatile organic compounds or analytes to different sensors using one or multiple differentiation and acceleration mechanisms such as (A) electrodes 342, 344, (B) electrodes 542, 544 and/or (C) heater 642, cooling devices 644.

Gas sources 1152, 54, 1156 comprise various sources for the gas atmosphere above culture 42. Each of gas sources 1152, 1154, 1156 includes a valve under the control of controller 1250. Pump 1158 comprises a device to pump a selected gas or gases from sources 1152, 1154, 1156 to the volume or space above culture 42, whether it be in the upper chamber 28 or into the space above culture 42 with a lower chamber 22. Controller 1250 outputs control signals to output a selected mixture of gases. Controller 1250 outputs control signals to control pump 1158 to control the rate at which such gases or mixture of gases are provided are to the space above surface 43 of culture 42.

Controller 1250 may control the mixture and rate of the supply of gas to create an atmosphere that promotes or inhibits growth of certain cell types, to lower atmospheric pressure to increase a mass fraction of volatile organic compounds and/or to introduce reactants (such as other VOCs) that react with the volatile organic compounds emitted by culture 42 to produce analytes that may be better detected by sensors 232. In one implementation, controller 1250 controls the gas provided system 1120 to promote or inhibit the growth of certain cell types by controlling the fraction of carbon dioxide and oxygen in the atmosphere in which the cells of culture 42 grow. Controller 1250 may adjust content of the atmosphere to increase the growth and production about organic compound by certain cells and decrease that of others. In one implementation, a shift in the cells' volatile organic compound signature as a function of their atmospheres content may be used by controller 1250 as a metric to identify cells. In some implementations, controller 1250 may lower the atmospheric pressure such that volatile organic compounds or at a larger effective concentration to increase the binding rate of volatile organic compounds to the surfaces of sensors 232, increasing sensitivity. The introduction of reactive compounds into the gas mixture by controller 1250 used to produce other compounds that produce stronger signals on sensors 232 to increase sensitivity.

Culture media sources 1162, 1164, 1166 comprise different sources for different media content or solutions. Each of sources 1162, 1164, 1166 includes a valve under the control of controller 1250. Pump 1168 comprises a device to pump a selected liquid or solid medium or media from sources 1162, 1164, 1166 to the culture 42. Controller 1250 outputs control signals to output a selected mixture of media. Controller 1250 outputs control signals to control pump 1168 to control the rate at which such media is provided to culture 42.

Controller 1250 outputs control signals control the mixture of media and the rate at which the mixture is provided to culture 42 by pump 1168 precisely control the culture 42 in which the cells grow and by which volatile organic compounds are produced. In one implementation, controller 1250 precisely controls (in time and/or concentration) the culture 42 to facilitate automatic and highly reproducible cell culturing. In some implementations, controller 1250 introduces pharmaceuticals to alter the metabolism and production of volatile organic compound by the cells in the culture 42. In some implementations, a cell's VOC signature as a function of media content may be utilized by controller 1250 as another metric to identify cells. In yet other implementations, controller 1250 may introduce (from one of sources 1162, 1164, 1166) that react with metabolites produced by the cells creased the volatility of the metabolites and/or increase the sensor response.

In one implementation, controller 1250 utilizes signals from each of sensors 232 as feedback adjustably control the operational parameters of volatile organic compound acceleration and differentiation by system 1120. For example, based upon signals or feedback from sensors 232, controller 1250 output control signals adjusting the electric fields provided by the different electrode pairs, electrode pairs 342, 344, and electrode pairs 542, 544. Based upon such feedback, controller 1250 may output control signals adjusting the operational settings of heater 642 and/or the operational settings of the individual cooling devices 644. Based upon feedback from sensors 232, controller 1250 may adjust the gas atmosphere above culture 42 by selectively opening and closing the valves of sources 1152, 1154, 1156 and/or the rate at which pump 1158 is operating. Likewise, based upon feedback from sensors 232, controller 1250 may adjust the media of culture 42 by selectively opening and closing the valves of sources 1162, 1164, 1166 and/or the rate at which pump 1168 is operating.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An apparatus comprising:
   a lower chamber to contain a culture that emits a volatile organic compound;
   an upper chamber;
   a sensor within the upper chamber;
   a transport accelerator to accelerate transport of the volatile organic compound in the lower chamber towards the sensor, wherein the transport accelerator comprises:
   a first electrode located within the lower chamber to extend above the culture; and
   a second electrode proximate the sensor, wherein the first electrode and the second electrode cooperate to form an electric field accelerating transport of the volatile organic compound towards the sensor.

2. The apparatus of claim 1, wherein the first electrode is one of a series of first electrodes vertically extending along the lower chamber.

3. The apparatus of claim 1 further comprising a permeable membrane extending between the lower chamber and the upper chamber, wherein the permeable membrane comprises reactive elements to convert the volatile organic compound to a different compound.

4. The apparatus of claim 1, further comprising a gas selective permeable membrane extending between the lower chamber and the upper chamber, wherein the gas selective permeable membrane is permeable to first volatile organic compound and is impermeable to second volatile organic compound.

5. The apparatus of claim 1, further comprising:
a culture media source;
a pump connected to a culture media source and the lower chamber; and
a controller to control the pump so as to selectively pump a culture media from the culture media source into the lower chamber based upon signals from the sensor.

6. The apparatus of claim 1, further comprising:
a gas source;
a pump connected to the gas source and the upper chamber; and
a controller to control the pump so as to selectively pump a gas from the gas source into the upper chamber based upon signals from the sensor.

7. The apparatus of claim 1, wherein the upper chamber comprises a first compartment containing the sensor and a second compartment isolated from the first compartment and containing a second sensor.

8. The apparatus of claim 1, further comprising:
a second sensor within the upper chamber;
a second transport accelerator to accelerate transport of a second volatile organic compound emitted by the culture in the lower chamber towards the second sensor such that transport of the second volatile organic compound is biased towards the second sensor as compared to the first sensor.

9. An apparatus comprising:
a lower chamber to contain a culture that emits a volatile organic compound;
an upper chamber;
a sensor within the upper chamber;
a transport accelerator to accelerate transport of the volatile organic compound in the lower chamber towards the sensor, wherein the transport accelerator comprises:
a first electrode tube located within the lower chamber to extend below a surface of the culture;
a second electrode located above the surface of the culture and having an aperture above the first electrode tube, the first electrode tube and the second electrode cooperating to form an electric field to form a spray.

10. The apparatus of claim 9 further comprising a permeable membrane extending between the lower chamber and the upper chamber, wherein the permeable membrane comprises reactive elements to convert the volatile organic compound to a different compound.

11. The apparatus of claim 9, further comprising a gas selective permeable membrane extending between the lower chamber and the upper chamber, wherein the gas selective permeable membrane is permeable to first volatile organic compounds and is impermeable to second volatile organic compounds.

12. The apparatus of claim 9 further comprising:
a culture media source;
a pump connected to a culture media source and the lower chamber; and
a controller to control the pump so as to selectively pump a culture media from the culture media source into the lower chamber based upon signals from the sensor.

13. The apparatus of claim 9 further comprising:
a gas source;
a pump connected to the gas source and the upper chamber; and
a controller to control the pump so as to selectively pump a gas from the gas source into the upper chamber based upon signals from the sensor.

14. The apparatus of claim 9, wherein the upper chamber comprises a first compartment containing the sensor and a second compartment isolated from the first compartment and containing a second sensor.

15. The apparatus of claim 9 further comprising:
a second sensor within the upper chamber;
a second transport accelerator to accelerate transport of a second volatile organic compound emitted by the culture in the lower chamber towards the second sensor such that transport of the second volatile organic compound is biased towards the second sensor as compared to the first sensor.

16. An apparatus comprising:
a lower chamber to contain a culture that emits a volatile organic compound;
an upper chamber;
a sensor within the upper chamber;
a transport accelerator to accelerate transport of the volatile organic compound in the lower chamber towards the sensor, wherein the transport accelerator comprises:
a first temperature control element proximate the culture, the first temperature control element being adjustable to provide a first temperature proximate the culture; and
a second temperature control element proximate the sensor, the second temperature control element being adjustable to provide a second temperature proximate the culture, the second temperature being different than the first temperature to form a temperature gradient to accelerate the transport of the volatile organic compound in the lower chamber towards the sensor;
a first electrode tube located within the lower chamber to extend below a surface of the culture; and
a second electrode located above the surface of the culture and having an aperture above the first electrode tube, the first electrode tube and the second electrode cooperating to form an electric field to form a spray.

17. The apparatus of claim 16, further comprising a permeable membrane extending between the lower chamber and the upper chamber, wherein the permeable membrane comprises reactive elements to convert the volatile organic compound to a different compound.

18. The apparatus of claim 16, further comprising a gas selective permeable membrane extending between the lower chamber and the upper chamber, wherein the gas selective permeable membrane is permeable to first volatile organic compounds and is impermeable to second volatile organic compounds.

19. The apparatus of claim 16, further comprising:
a second sensor within the upper chamber;
a second transport accelerator to accelerate transport of a second volatile organic compound emitted by the culture in the lower chamber towards the second sensor such that transport of the second volatile organic compound is biased towards the second sensor as compared to the first sensor.

* * * * *